US007751888B1

(12) United States Patent
Schecter

(10) Patent No.: US 7,751,888 B1
(45) Date of Patent: Jul. 6, 2010

(54) SYSTEMS AND METHODS FOR DELIVERING STIMULATION PULSES USING AN IMPLANTABLE CARDIAC STIMULATION DEVICE

(75) Inventor: Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 585 days.

(21) Appl. No.: 11/467,833

(22) Filed: Aug. 28, 2006

(51) Int. Cl.
A61N 1/365 (2006.01)
A61N 1/36 (2006.01)

(52) U.S. Cl. .......................................... 607/17; 607/28
(58) Field of Classification Search ................. 607/9, 607/17, 28
See application file for complete search history.

(56) References Cited

U.S. PATENT DOCUMENTS

| 5,673,704 | A  | * | 10/1997 | Marchlinski et al. ........ 600/552 |
| 6,233,484 | B1 |   | 5/2001  | Ben-Haim et al. |
| 6,236,887 | B1 |   | 5/2001  | Ben-Haim et al. |
| 6,263,242 | B1 |   | 7/2001  | Mika et al. |
| 6,292,693 | B1 |   | 9/2001  | Darvish et al. |
| 6,317,631 | B1 |   | 11/2001 | Ben-Haim et al. |
| 6,330,476 | B1 |   | 12/2001 | Ben-Haim et al. |
| 6,363,279 | B1 |   | 3/2002  | Ben-Haim et al. |
| 6,370,430 | B1 |   | 4/2002  | Mika et al. |
| 6,424,866 | B2 |   | 7/2002  | Mika et al. |
| 6,463,324 | B1 |   | 10/2002 | Ben-Haim et al. |
| 6,512,952 | B2 |   | 1/2003  | Stahmann et al. |
| 6,587,721 | B1 |   | 7/2003  | Prutchi et al. |
| 6,628,988 | B2 |   | 9/2003  | Kramer et al. |
| 6,643,546 | B2 |   | 11/2003 | Mathis et al. |
| 6,725,093 | B1 |   | 4/2004  | Ben-Haim et al. |
| 6,760,622 | B2 |   | 7/2004  | Helland et al. |
| 6,922,587 | B2 |   | 7/2005  | Weinberg |
| 7,010,347 | B2 |   | 3/2006  | Schecter |
| 7,065,400 | B2 |   | 6/2006  | Schecter |
| 7,283,873 | B1 | * | 10/2007 | Park et al. ..................... 607/16 |
| 2002/0055764 | A1 |   | 5/2002  | Malonek et al. |
| 2004/0049238 | A1 | * | 3/2004  | Jarverud ..................... 607/17 |
| 2004/0220631 | A1 |   | 11/2004 | Burnes et al. |
| 2005/0182447 | A1 | * | 8/2005  | Schecter ........................ 607/2 |
| 2006/0247698 | A1 | * | 11/2006 | Burnes et al. .................. 607/9 |

FOREIGN PATENT DOCUMENTS

WO       0027468        5/2000

(Continued)

OTHER PUBLICATIONS

Cleland J.G.F. et al. (on behalf of The CARE-HF study Steering Committee and Investigators), "The CARE-HF study (CArdiac REsynchronisation in Heart Failure study): Rationale, Design and End-points," Eur J Heart Failure 2001; 3: 481-489.

Primary Examiner—Carl H. Layno
Assistant Examiner—Tammie K Heller

(57) ABSTRACT

Techniques are described for delivering inotropic electrical therapy to myocardial tissue using an implantable cardiac stimulation device such as a pacemaker. In one example, electrical stimulation is applied by a pacemaker to the heart of a patient while taking into account dynamic trans-cardiac impedance waveforms measured within the patient. In another example, a series of subthreshold inotropic stimulation pulses are delivered just prior to delivery of a suprathreshold depolarizing pulse that triggers systole. Additional subthreshold inotropic stimulation pulses can also be delivered following the suprathreshold pulse. Preferably, the magnitudes of the inotropic pulses are incrementally increased prior to systole then decremented thereafter, thereby gradually recruiting myocardium that has differing thresholds for depolarization. Both techniques seek to improve myocardial contractility of diseased tissue by improving calcium flux. Both techniques may additionally exploit the use of "multi-dimensional forced fusion", described herein.

29 Claims, 11 Drawing Sheets

FOREIGN PATENT DOCUMENTS

| | | | |
|---|---|---|---|
| WO | 0027472 | | 5/2000 |
| WO | 0057952 | | 10/2000 |
| WO | 0057952 | A1 | 10/2000 |
| WO | 0158518 | A2 | 8/2001 |
| WO | 0158518 | A3 | 8/2001 |
| WO | 2005018570 | A2 | 3/2005 |
| WO | 2005018570 | A3 | 3/2005 |

* cited by examiner

SYSTEMS AND METHODS FOR DELIVERING STIMULATION PULSES USING AN IMPLANTABLE CARDIAC STIMULATION DEVICE

FIELD OF THE INVENTION

The invention generally relates to implantable cardiac stimulation systems for use in stimulating the heart and, in particular, to techniques for delivering inotropic stimulation, i.e. stimulation intended to affect the contractility of the heart.

BACKGROUND OF THE INVENTION

A variety of medical conditions affect the ability of heart muscle to properly contract in response to electrical stimulus—either intrinsic stimulus generated by the sinus node and conduction system of the heart or therapeutic pacing pulses delivered by a pacemaker or other implantable cardiac stimulation device. In particular, various cardiomyopathies of differing etiologies can affect myocardial contractility, and the temporal relationships of motion/contractility of various regions (dysynchrony). These effects can be secondary to a combination of primary disturbances in electrical conduction and pathologic myocardial tissue.

Cardiomyopathy, i.e. "heart muscle disease", pertains to the deterioration of the function of the myocardium. Cardiomyopathy often results in heart failure as the pumping efficiency of the heart is diminished. Patients with cardiomyopathy are often at risk for arrhythmia and/or sudden cardiac death (typically due to ventricular fibrillation). Some cardiomyopathies are deemed extrinsic, whereas others are intrinsic.

Extrinsic cardiomyopathies are those in which the primary pathology is outside the myocardium itself and include such cardiomyopathies as ischemic cardiomyopathy, hypertensive cardiomyopathy, valvular cardiomyopathy, inflammatory cardiomyopathy and cardiomyopathy secondary to systemic diseases. Of these, the most common is ischemic cardiomyopathy, which pertains to weakness in the myocardium due, e.g., to coronary artery disease. Patients with ischemic cardiomyopathy often have a history of acute myocardial infarction (i.e. heart attack), although chronic ischemia can cause sufficient damage to the myocardium to cause a clinically significant cardiomyopathy even in the absence of myocardial infarction. Typically, the area of the heart affected by a myocardial infarction becomes necrotic and is replaced by scar tissue (fibrosis). Fibrotic tissue is "akinetic", i.e. it no longer functions as muscle and hence does not contribute to the heart's pumping function. In many cases, the affected side of the heart (i.e. the left side or the right side) will go into failure. Heart failure that is sufficiently severe is referred to as congestive heart failure (CHF), which is a frequent cause of mortality in elderly patients. Intrinsic cardiomyopathy, in contrast, pertains to a weakness in the myocardium that is not due to an identifiable external cause.

Intrinsic cardiomyopathy can arise due to certain infections (including Hepatitis C, Coxsackie viruses), and various genetic and idiopathic (i.e., unknown) causes as well as from alcohol and drug use. Exemplary types of intrinsic cardiomyopathies include dilated cardiomyopathy, hypertrophic cardiomyopathy, arrhythmogenic right ventricular cardiomyopathy and restrictive cardiomyopathy.

In general, with diseased myocardium, there is a combination of denervation or impairment of the normal physiologic conduction system, myocardial stunning, hibernation and cell death. (Myocardial stunning is the phenomenon in which brief, reversible episodes of ischemia leave a prolonged depression of cardiac function that recovers only slowly over several hours or days.) Myocardial stunning, hibernation and cell death lead to hypocontractility, i.e. reduced contractility. Reduced contractility often results in a loss of cardiac output and also a lack of synchronous depolarization, i.e. a lack of coordination between the left and right chambers, atrial and ventricular chambers or within the left ventricular chamber itself (intra-ventricular dysynchrony). These impairments are often segmental, i.e. regional rather than global, especially in patients with ischemic heart disease.

As can be appreciated, the impairment in myocardial contractility arising from cardiomyopathy or other causes can significantly impair the functioning of the heart, leading to debilitated lifestyle and, in all too many cases, death. Accordingly, it would be highly desirable to remedy or mitigate any loss of contractility and reduce dysynchronous electro-mechanical activation. Various pharmacological treatments are available but these tend to affect the entire myocardium and do not target particular parts of the heart that may be impaired, i.e. the treatments do not specifically address segmental impairments. Many patients with impaired myocardial contractility have pacemakers, implantable cardioverter-defibrillators (ICDs) or other medical devices implanted therein that permit electrical stimulation to be selectively delivered to particular portions or chambers of the heart. Accordingly, techniques have been developed that seek to improve myocardial contractility using such devices by delivering non-pharmacologic inotropic therapy (NPIT) and improving synchronous electro-mechanical activation with Cardiac Resynchronization Therapy (CRT). CRT is the sum and substance of currently implanted biventricular pacing systems. NPIT is not yet widely available and still is under investigational study. However, a wealth of literature exists, which demonstrate the benefits of CRT for improving heart failure symptoms and even reducing mortality (see, e.g., the "Cardiac Resynchronization in Heart Failure" study, i.e. the "CARE-HF" study, Cleland et al. on behalf of *The CARE-HF study Steering Committee and Investigators*, "The CARE-HF study (CArdiac REsynchronisation in Heart Failure study): Rationale, Design and End-points, Eur Heart J, 2001; 3: 481-489). CRT is also discussed in, for example, U.S. Pat. No. 6,643,546 to Mathis, et al., entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing".

Techniques for delivering non-excitory inotropic stimulation to the heart in an effort to improve contractility are just emerging. See, for example, U.S. Pat. No. 6,233,484 to Ben-Haim et al. entitled "Apparatus and Method for Controlling the Contractility of Muscles" and related patents and patent applications of Impulse Dynamics N.V. The techniques described therein generally involve delivering relatively high voltage electrical stimulation pulses during a refractory period (during which the myocardium is not capable of contracting in response to electrical stimulation). The stimulation pulses are apparently intended to enhance calcium flux so as to improve contractility such that subsequent contractions are more hemodynamically effective.

Although refractory period-based inotropic techniques appear to be promising, it is believed that effective inotropic treatment can also be obtained by selectively delivering electrical stimulation outside of the refractory period, and it is to this end that certain aspects of the present invention are directed. In particular, it is desirable to provide techniques for applying subthreshold inotropic stimulation (i.e. stimulation below a threshold sufficient to trigger depolarization of the myocardium) outside the refractory period for the purposes of improving myocardial contractility. Among other potential advantages, subthreshold stimulation generally uses less power than the comparatively high voltage refractory period-based inotropic stimulation and hence does not significantly deplete battery power. Other aspects of the invention pertain to techniques for delivering suprathreshold inotropic stimulation (i.e. electrical stimulation above the threshold necessary to trigger depolarization) outside refractory periods and at the appropriate times to reduce dysynchronous activation patterns. Still other aspects of the invention are applicable to providing improvements to refractory period-based inotropic stimulation. Thus, the technologies described offer a combined approach to regionally improve contractility and reduce electromechanical dysynchrony in territories that have pathologic contractility and conductivity and allow normal tissue to function unaffected. These device based therapies are implemented when and where needed based, e.g., on repeated measurements of impedance based metrics that reflect contractile and conductive cardiac properties.

SUMMARY

In accordance with a first general embodiment, techniques are provided for delivering inotropic electrical stimulation or other forms of electrical stimulation to the heart of a patient using an implantable cardiac stimulation device that takes into account dynamic impedance waveforms. The dynamic impedance waveforms represent electrical impedance as a function of time (i.e. Z(t)). During systole, the impedance along a direction of contraction of myocardial tissue increases due to an increase in myocardial thickness during contraction and due to a reduction in blood volume and perhaps due to other factors. The dynamic impedance waveform of healthy myocardial tissue differs from the corresponding waveforms of diseased or ischemic tissues, i.e. tissues with impaired contractility. Typically, the dynamic impedance waveform of diseased tissues exhibits a less significant change in impedance during systole than that of healthy tissue.

In one example, information pertaining to dynamic impedance waveforms within the heart of the patient (i.e. $Z_{patient}(t)$) is measured or otherwise obtained by the implanted device. Information pertaining to dynamic impedance waveforms within the healthy or eucontractile hearts (i.e. $Z_{eucontractile}(t)$) is input. $Z_{eucontractile}(t)$ can be obtained, e.g., from data collected from patients implanted with devices who have had reverse remodeling and no longer suffer from cardiomyopathy. Alternatively or additionally, data can be derived from devices implanted in patients with primary electrical disturbances (e.g. long QT syndrome, Brugada syndrome) with structurally normal hearts. In any case, electrical stimulation is then delivered to the heart of the patient by the device based on a comparison of $Z_{patient}(t)$ and $Z_{eucontractile}(t)$. Preferably, the electrical stimulation is delivered so as to reduce or minimize a difference between $Z_{patient}(t)$ and $Z_{eucontractile}(t)$. It is believed that stimulation that tends to reduce the difference between $Z_{patient}(t)$ and $Z_{eucontractile}(t)$ likewise tends to improve contractility within the myocardial tissue being stimulated, i.e. the stimulation is inotropic. In one particular example, $Z_{patient}(t)$ is compared against $Z_{eucontractile}(t)$ to determine parameters that minimize an average difference between $Z_{patient}(t)$ and $Z_{eucontractile}(t)$ throughout systole. In another example, an integral of $Z_{eucontractile}(t)$ (i.e. $\int Z_{patient}(t) dt$) is compared against an integral of $Z_{eucontractile}(t)$ (i.e. $\int Z_{eucontractile}(t) dt$) to determine parameters that minimize a measure of incongruence of the integrals during systole. Preferably, these procedures are applied along each of a plurality of stimulation vectors, i.e. dynamic impedance is measured between each of a set of pairs of pacing/sensing electrodes, so as to address segmental contractility deficits. Note that the parameters set forth herein are merely exemplary and are by no means restricted to integration techniques applied to the dynamic impedance waveform. Other indices derived from impedance data may instead be implemented including, but not limited to, measurements of first and second order derivatives of the impedance waveform during different time periods of the cardiac cycle. Importantly, the parameters do not necessarily need to be based on $Z_{eucontractile}(t)$ but can be based on monitoring changes in any impedance based metric while the pacing modalities described herein are active.

In one particular implementation, parameters defining the characteristics of electrical stimulation, such as voltage, current, polarity, timing, stimulation frequency and the particular electrodes used to deliver the stimulation (i.e. the stimulation vector) are automatically adjusted or varied by the implanted device. Resulting dynamic impedance waveforms $Z_{patient}(t)$ occurring within the patient are measured and compared against a template representative of the dynamic impedance waveforms of healthy hearts $Z_{eucontractile}(t)$ so as to determine a set of parameters associated with any or all stimulation vectors that minimizes the average difference between $Z_{patient}(t)$ and $Z_{eucontractile}(t)$ or that minimizes a difference between integrals of $Z_{patient}(t)$ and $Z_{eucontractile}(t)$. That is, the parameters are adaptively adjusted to minimize differences between the dynamic impedance waveforms of the patient and those of healthy persons. (Additionally, or alternatively, parameters can be determined that optimize other impedance measurements such as positive and negative dZ/dt, dZ'/dt). Thereafter, further delivery of stimulation is performed using the adaptively adjusted set of parameters so as to remodel the myocardium. This procedure may be periodically repeated to further adjust the parameters to take into account progression or regression of cardiomyopathies, new episodes of ischemia, myocardial stunning, etc.

Various impedance based indices may be derived from quantitative analysis of the dynamic impedance waveform and used alone or in combination for such comparisons. These indices provide the system with a physiologically relevant parameter that reflects the cardiac pathologic state. Quantitative analysis of the dynamic impedance waveform derived from various electrode combinations is suitable for such a technique as this data is representative of the contractile state and timing of contraction.

Note that, depending upon the needs of the particular patient and the programming of the device, the inotropic stimulation thus delivered may be subthreshold, suprathreshold or a combination of the two. Furthermore, the inotropic stimulation may be selectively delivered during a refractory period or during non-refractory periods, again depending upon the patient, regional properties of any given innervated region and the programming of the device. Insofar as inotropic stimulation delivered during refractory periods is concerned, the invention provides a technique for automatically adjusting the parameters defining such non-excitory stimulation so as to potentially improve its inotropic effect where and when needed. Insofar as inotropic stimulation delivered outside refractory periods is concerned, such stimulation may include both subthreshold and suprathreshold components, delivered during systole and/or diastole. In particular, depending upon the needs of the patient, suprathreshold stimulation may be selectively delivered during systole along particular stimulation vectors while timed to trigger local depolarization that fuses with intrinsic and more global myocardial depolarization. That is, the suprathreshold inotropic stimulation triggers an evoked response that fuses with an ongoing intrinsic depolarization arising due to natural pacing signals generated by the sinus node and intact portions of the conduction system. This procedure is referred to herein as "multidimensional forced fusion" (MDF). Multidimensional refers to both spatial and temporal components of electromechanical activation, i.e. MDF refers to the delivery of one or more suprathreshold pulse(s) triggering localized depolarizations that fuse with intrinsic depolarization in a synchronous fashion as to optimize both spatial and temporal aspects of myocardial electro-mechanical activation. This synchronous, inotropic pacing modality thereby seeks to minimize anisotropic properties in contractility and electro-mechanical dysynchrony, leading to multidimensional forced fusion. Thus, this technology serves to reduce anisotropic contractile properties and dysynchronous electromechanical activation. MDF represents one particularly promising technique for modifying a patient's dynamic impedance waveform to more closely match the dynamic impedance waveform of healthy hearts thereby restoring normal contractility and mechanical synchrony as is described in more detail below.

In accordance with a second general embodiment of the invention, techniques are provided for delivering a series of subthreshold stimulation pulses to the heart of a patient along with at least one suprathreshold pulse so as to achieve an inotropic effect, appropriately timed relative to depolarization of normally functioning myocardium. In one example, a series of subthreshold stimulation pulses are delivered prior to systole. At least one suprathreshold stimulation pulse is then delivered to the heart to trigger systole and then a series of additional subthreshold pulses are delivered following the suprathreshold pulse. In other examples, subthreshold pulses are only delivered just prior to the suprathreshold pulse or only just following the suprathreshold pulse. It is believed that, in at least some patients, the subthreshold pulses delivered before and/or after the suprathreshold pulse tend to improve myocardial contractility during systole. Preferably, the initial set of subthreshold pulses delivered prior to systole includes high frequency pulses having incrementally increasing pulse magnitudes. The pulse magnitudes increase until a depolarization threshold is eventually exceeded, thus providing at least one suprathreshold pulse that triggers depolarization. The subsequent set of subthreshold pulses delivered following the suprathreshold pulse are high frequency pulses having incrementally decreasing pulse magnitudes (i.e. decrementing magnitudes). The pulse magnitudes decrease throughout systole and during at least a portion of a subsequent period of diastole. Such incremental and/or decremental high frequency pacing algorithms may be modified as appropriate. By way of example, an initial decremental reduction in pulse magnitude followed by an incremental increase in pulses magnitudes may be beneficial in specific clinical scenarios.

In one particular example, the aforementioned dynamic impedance waveform techniques are employed to adjust the parameters defining the subthreshold pulses so as to improve their inotropic effect. Further, the suprathreshold pulse delivered along with the subthreshold pulses may be timed and directed so as to achieve MDF with an intrinsic depolarization, in accordance with techniques already summarized.

System and method implementations of these and other exemplary techniques are described herein.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Inotropic Stimulation Controlled Using Dynamic Impedance Waveforms

Figure 1:
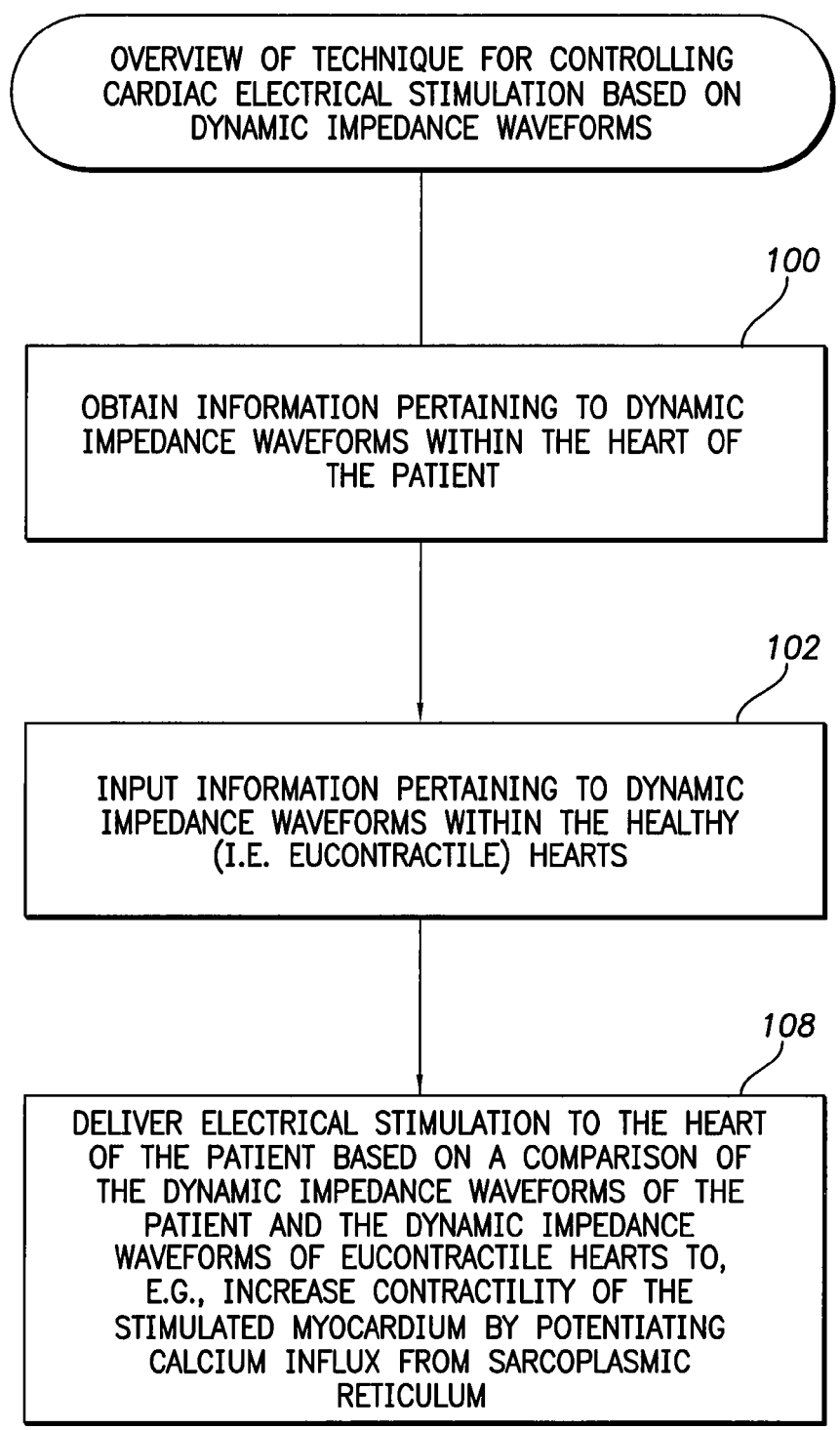
FIG. 1 is a flow chart providing an overview of a general technique for controlling cardiac electrical stimulation based on dynamic impedance waveforms.

Referring first to FIG. 1, an overview of the general technique for controlling inotropic stimulation based on dynamic waveforms will be provided. The technique is performed by an implantable cardiac stimulation device such as a pacemaker or ICD (herein generally referred to as a "pacer/ICD")

or other appropriate implantable medical device. Beginning at step 100, information pertaining to dynamic impedance waveforms within the heart of the patient is measured or otherwise obtained by the pacer/ICD. In one example, techniques described in U.S. Pat. No. 7,010,347 to Schecter, entitled "Optimization of Impedance Signals for Closed Loop Programming of Cardiac Resynchronization Therapy Devices" are employed to obtain information representative of dynamic impedance waveforms within the heart of the patient. At step 102, information pertaining to dynamic impedance waveforms within the healthy (i.e. "eucontractile") hearts are input, preferably from internal memory of the pacer/ICD.

The term "eucontractile" is a nonstandard term used herein to generally convey that the dynamic impedance waveforms generated are from the chambers of hearts with normal contractility and synchronous electromechanical activation. By way of example, such eucontractile impedance waveforms can be derived from structurally normal hearts and/or hearts that have had reverse remodeling after recovering from cardiomyopathy. In order to compile such template impedance waveforms for comparative purposes, this data is acquired from patients implanted with devices that are no longer pathologic or are structurally normal with primary electrical disturbances and not myopathic (e.g. Brugada syndrome, long QT syndrome). The techniques of the invention seek to render the dynamic impedance waveform from a patient's heart as eucontractile as possible.

In one example, dynamic impedance waveforms from a population of healthy patients are obtained in advance using the techniques of U.S. Pat. No. 7,010,347. These waveforms are averaged or otherwise combined into a waveform template (referred to herein as a "eucontractile waveform template"), which is stored in the memory of the pacer/ICD following device implant. In this regard, note that many patients with pacer/ICDs do not have ischemic heart disease or cardiomyopathy and hence represent a population of patients from which eucontractile data can be readily obtained for use in creating the eucontractile waveform template.

Figure 2:
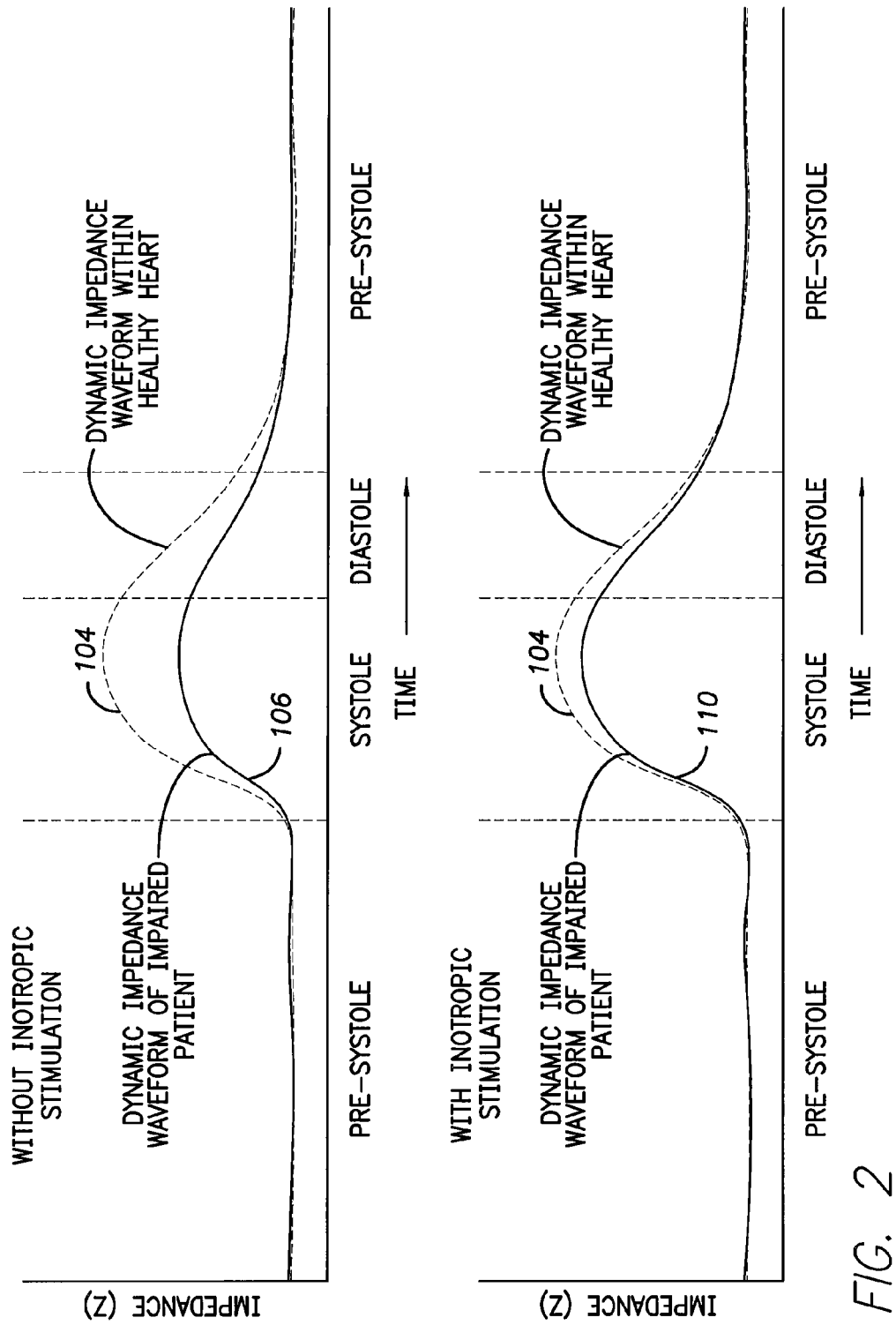
FIG. 2 is a graph illustrating exemplary dynamic impedance waveforms exploited using the general technique of FIG. 1.

As already summarized, the impedance along a direction of contraction of myocardial tissue increases during systole due to an increase in myocardial thickness that occurs during contraction and due to a reduction in blood volume and perhaps due to other factors. The dynamic impedance waveform of healthy (i.e. eucontractile) myocardial tissue $Z_{eucontractile}(t)$ differs from the corresponding impedance waveforms of diseased or ischemic tissues, i.e. tissues with impaired contractility. Typically, the dynamic impedance waveform of diseased tissues exhibits a less significant change in impedance during systole than that of healthy tissue. This is illustrated by the upper graph of FIG. 2 by way of a eucontractile dynamic impedance waveform 104 and the dynamic impedance waveform of an impaired patient 106 taken along a direction of myocardial contraction. As can be seen, impedance increases during systole and then decreases during diastole. The dynamic increase in impedance occurring during systole is significantly less in the impaired patient than in the healthy patient due to hypocontractility. Note that the graphs of FIG. 2 are stylized representations of dynamic impedance waveforms shown on an arbitrary scale, which are provided to illustrate concepts of the invention. The graphs do not represent actual clinical data. Dynamic impedance waveforms within actual patients may differ in shape and magnitude from those illustrated. Note also that a static or baseline component of impedance may vary based on voltage delivered, but this likely has no physiological significance insofar as differences in myocardial contractility are concerned.

Returning to FIG. 1, at step 108 the pacer/ICD delivers electrical stimulation to the heart of the patient based on a comparison of the dynamic impedance waveforms of the patient and the dynamic impedance waveforms of healthy persons to, e.g., increase contractility of the stimulated myocardium. The contractility may increase as a result of potentiating calcium influx from sarcoplasmic reticulum or other factors. (The sarcoplasmic reticulum is a component of myocardial cells that stores and releases calcium.) Preferably, stimulation is controlled so as to reduce some measure of the difference between $Z_{patient}(t)$ and $Z_{eucontractile}(t)$. This is illustrated by the lower graph of FIG. 2. As can be seen, the dynamic impedance waveform 110 of the patient $Z_{patient}(t)$ now more closely approximates $Z_{eucontractile}(t)$ 104. It is believed that, by controlling stimulation to reduce the difference between $Z_{patient}(t)$ and $Z_{eucontractile}(t)$, effective inotropic stimulation is thereby achieved. That is, hypocontractility may be mitigated by selectively and repeatedly applying electrical stimulation in order to achieve a reduction in the difference between $Z_{patient}(t)$ and $Z_{eucontractile}(t)$ that will ultimately remodel the myocardium (i.e. reverse remodeling). Other advantages or benefits may potentially occur as well and so the benefit of this therapy regime is not necessarily limited to inotropic benefits.

Figure 3:
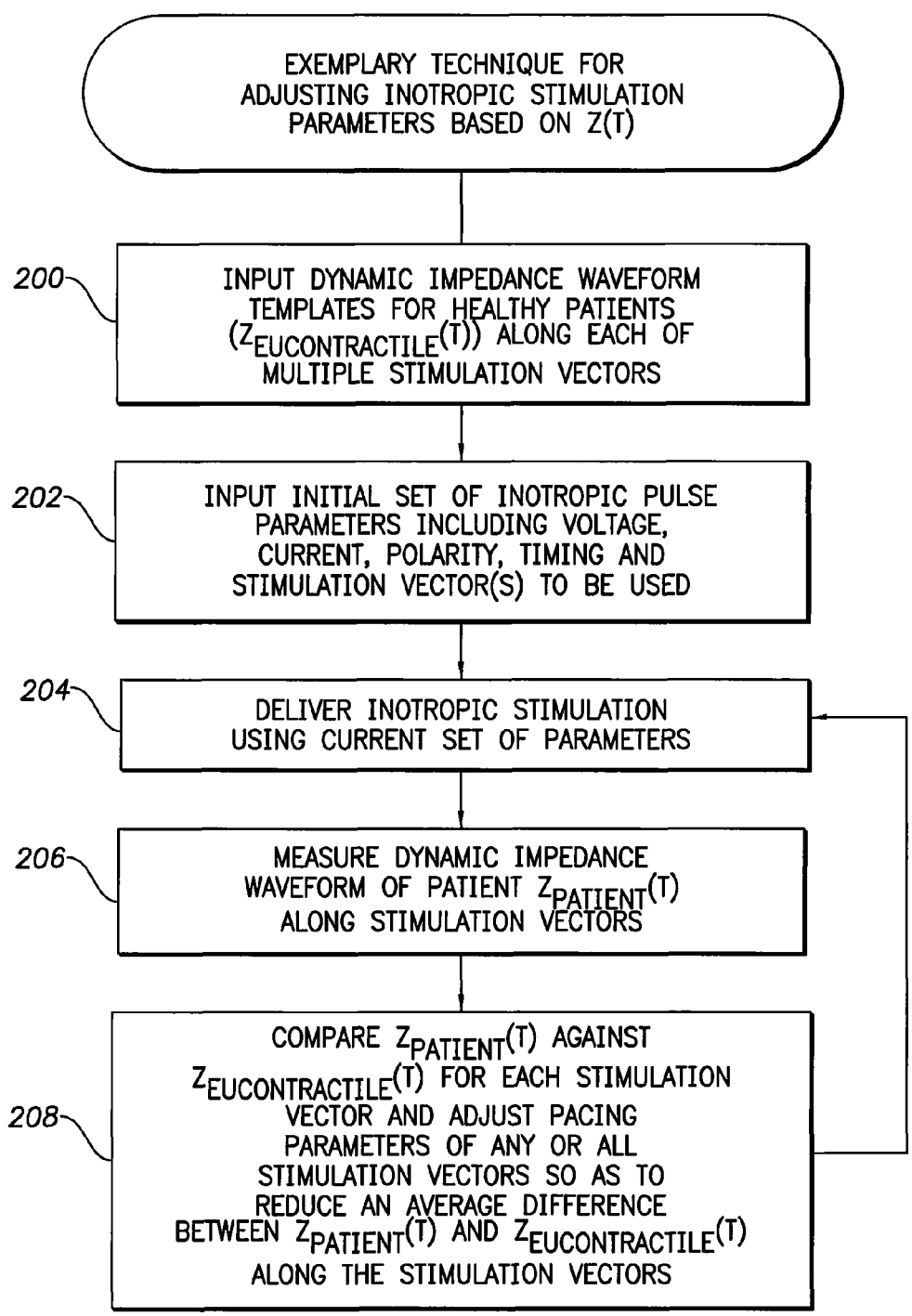
FIG. 3 is a flow chart illustrating a first exemplary technique for adaptively adjusting inotropic stimulation parameters based on dynamic impedance waveforms, in which dynamic impedance functions are compared.

FIG. 3 illustrates a first example of the general technique of FIGS. 1 and 2, which adaptively varies various stimulation parameters to find a set that minimizes a difference between $Z_{patient}(t)$ and $Z_{eucontractile}(t)$. Beginning at step 200, the pacer/ICD inputs dynamic impedance waveform templates obtained for healthy patients (i.e. $Z_{eucontractile}(t)$) along each of multiple stimulation vectors. That is, $Z_{eucontractile}(t)$ is measured within healthy persons along multiple stimulation vectors defined by different pairs of sensing/pacing electrodes. For example, $Z_{eucontractile}(t)$ may be separately measured between left ventricular (LV) tip and ring electrodes, right ventricular (RV) tip and ring electrodes, LV tip and LV tip electrodes, LV ring and RV ring electrodes, etc. Again, see the techniques described in U.S. Pat. No. 7,010,347. In some implementations, numerous sensing electrodes may be employed within the various heart chambers to increase the number and orientation of the stimulation vectors. See, for example, U.S. Pat. No. 6,760,622 to Helland, et al., entitled "Implantable Multi-Chamber Cardiac Stimulation Device with Sensing Vectors".

At step 202, the pacer/ICD inputs from memory an initial, default set of inotropic stimulation pulse parameters including voltage, current, polarity, timing and the particular stimulation vector(s) to be used. The default inotropic pulse parameters typically differ significantly from the default parameters used for conventional pacing pulses. For example, the inotropic parameters may specify subthreshold pulse voltages timed for delivery just before or after suprathreshold pacing pulses. As another example, the inotropic parameters may specify "suprathreshold" pulse voltages timed for delivery during refractory periods. As will be explained further below, the inotropic pulse parameters may also specify the parameters of an entire sequence or train of subthreshold pulses. In one particular example, the default inotropic parameters are parameters found to be effective in other patients having similar medical conditions to the patient to receive the therapy as determined, e.g., based on otherwise routine experimentation involving populations of like patients. Typically, the default inotropic parameters are programmed or loaded into the pacer/ICD following device implant along with other default operational parameters of the device, such as default pacing parameters.

At step 204, the pacer/ICD delivers inotropic stimulation using the currently loaded set of inotropic pulse parameters. Hence, if the parameters specify that a set of subthreshold inotropic pulses are to be delivered during systole using a particular set of stimulation vectors, then such stimulation is generated by the pacer/ICD and delivered to the heart of the patient by the appropriate set of electrodes implanted within the heart at that time. The inotropic stimulation is typically in addition to otherwise conventional pacing pulses that might be delivered. At step 206, the pacer/ICD measures the dynamic impedance waveform of patient $Z_{patient}(t)$ along the various stimulation vectors specified at step 200. Again, techniques described in U.S. Pat. No. 7,010,347 may be used. At step 208, the pacer/ICD then compares $Z_{patient}(t)$ against $Z_{eucontractile}(t)$ for each stimulation vector and adjusts the inotropic pulse parameters associated with any or all stimulation vectors in an attempt to reduce an average difference between $Z_{patient}(t)$ and $Z_{eucontractile}(t)$ along the various stimulation vectors. A variety of otherwise conventional mathematic techniques may be used quantify the amount of difference between or among the various dynamic impedance waveforms along the various stimulation vectors. (Techniques exploiting integrals are discussed below in connection with FIG. 4.) Processing then returns to step 204 where additional inotropic stimulation is delivered using the adjusted set of parameters. Steps 204-208 proceed in a loop to repeatedly and iteratively adjust the inotropic parameters in an effort to improve patient contractility by reducing the average difference between $Z_{patient}(t)$ and $Z_{eucontractile}(t)$ along the various stimulation vectors.

In this manner, an iterative and adaptive procedure is provided for optimizing inotropic stimulation parameters. In particular, the pacer/ICD is preferably programmed to select different stimulation vectors for delivery of the inotropic stimulation during initial iterations of the procedure so as to identify the particular stimulation vectors that have the greatest affect on contractility. Typically, these will be the vectors that are aligned with the direction of contraction of the hypocontractile myocardial tissues. By selecting particular stimulation vectors or combinations of stimulation vectors, multi-dimensional inotropic therapy is thereby achieved. Once the optimal stimulation vector(s) has been identified, the other parameters defining the inotropic stimulation pulse are then iteratively and adaptively adjusted to refine the efficacy of the pulses. Typically, the range of adjustment of the various parameters is constrained in advance. For example, to provide subthreshold inotropic pacing outside of refractory periods, the pulse voltage and current magnitudes are constrained to remain at subthreshold levels. As another example, to provide nonexcitory inotropic pacing within refractory periods, the pulse voltage and current magnitudes may exceed threshold levels, but the timing of those pulses is constrained to ensure the pulses are delivered within refractory periods.

In one example, this iterative procedure is performed continuously or at least very frequently to substantially continuously update the inotropic pulse parameters. Alternatively, the procedure may instead be performed only until further adjustments do not achieve significant gains in myocardial contractility or until some fixed number of iterations is compete. If so, the procedure is preferably reactivated periodically to adjust the inotropic parameters in response to changes within the patient, such as progression or regression of cardiomyopathy or the onset of additional episodes of cardiac ischemia. Indeed, detection of an episode of cardiac ischemia may be used to trigger activation of the procedure so as to promptly address any localized changes in contractility arising due to the ischemia. Techniques for detecting cardiac ischemia using a pacer/ICD are described in, e.g., U.S. patent application Ser. No. 10/603,429, entitled "System and Method for Detecting Cardiac Ischemia Using an Implantable Medical Device", of Wang et al.; U.S. patent application Ser. No. 10/603,398, entitled "System and Method for Detecting Cardiac Ischemia Based on T-Waves using an Implantable Medical Device", of Min et al.; and in U.S. patent application Ser. No. 11/394,724, of Ke et al. entitled "System and Method for Detecting Cardiac Ischemia in Real-Time using a Pattern Classifier Implemented within an Implantable Medical Device". Procedures for detecting progression or regression of cardiomyopathies may also be used to trigger the iterative procedure. See, for example, U.S. Pat. No. 6,922, 587 of Weinberg, entitled "System and Method for Tracking Progression of Left Ventricular Dysfunction Using Implantable Cardiac Stimulation Device". See, also, U.S. patent application Ser. No. 11/397,066 of Koh, entitled "QT-Based System and Method for Detecting and Distinguishing Dilated Cardiomyopathy and Heart Failure Using an Implantable Medical Device".

Figure 4:
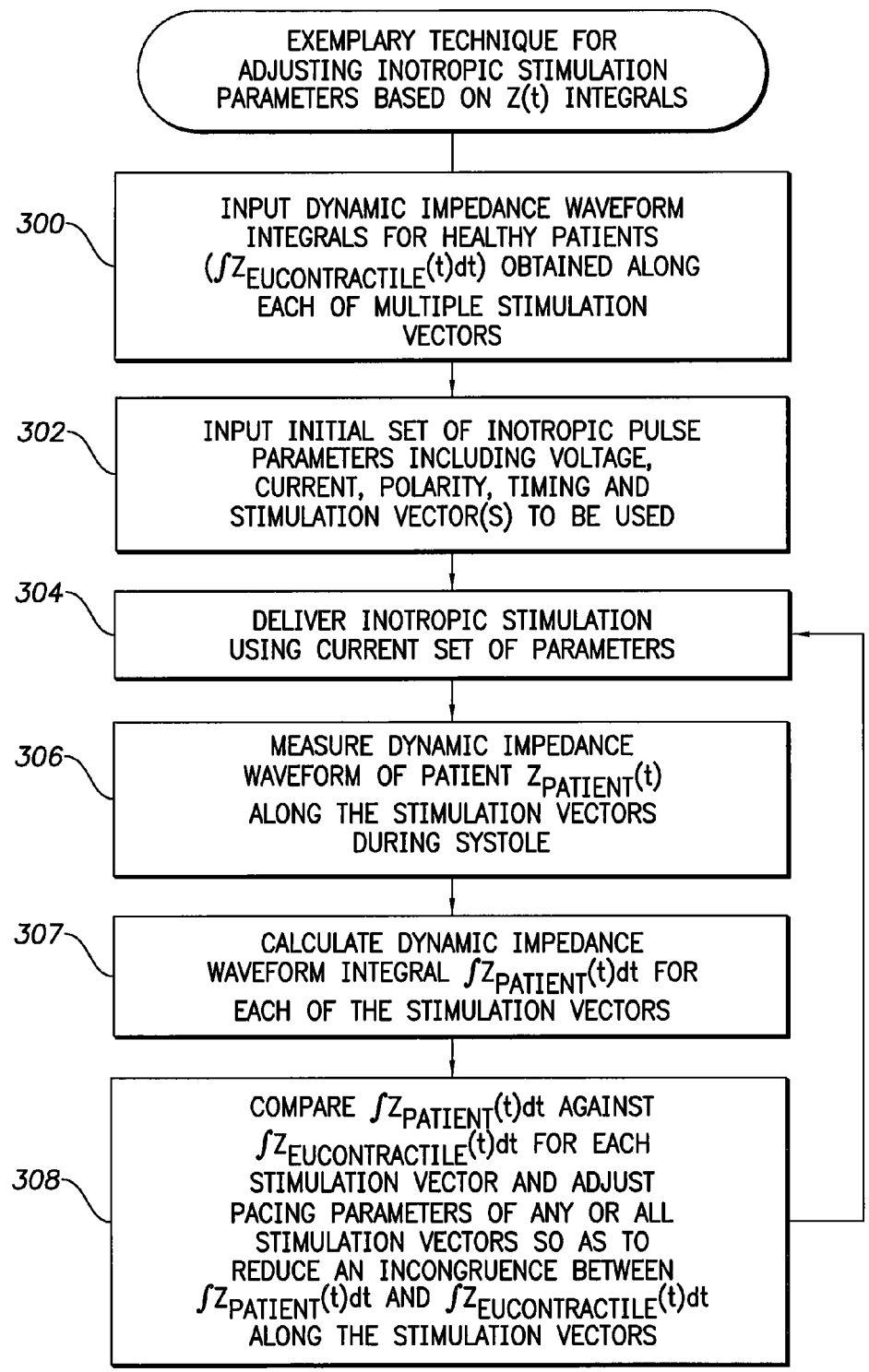
FIG. 4 is a flow chart illustrating a second exemplary technique for adaptively adjusting inotropic stimulation parameters based on dynamic impedance waveforms, in which integrals of dynamic impedance functions are compared.

FIG. 4 illustrates a second example of the general technique of FIGS. 1 and 2, which adaptively varies various stimulation parameters to find a set that minimizes a difference between integrals of $Z_{patient}(t)$ and $Z_{eucontractile}(t)$. As many of the steps of FIG. 4 are the same as FIG. 3, only pertinent differences are described in detail. Beginning at step 300, the pacer/ICD inputs dynamic impedance waveform integrals obtained for healthy persons (i.e. $\int Z_{eucontractile}(t)\, dt$) along each of multiple stimulation vectors. As above, $Z_{eucontractile}(t)$ is measured within healthy persons along multiple stimulation vectors. However, the $Z_{eucontractile}(t)$ values are then integrated with respect to time to obtain individual values representative of each dynamic waveform. At step 302, the pacer/ICD inputs from memory the initial, default set of inotropic stimulation pulse parameters to be used. These may be the same default values as described above. At step 304, the pacer/ICD delivers inotropic stimulation using the currently loaded set of pulse parameters and, at step 306, measures the resulting dynamic impedance waveform of patient $Z_{patient}(t)$ along the various stimulation vectors specified at step 300. At step 307, the pacer/ICD integrates each of the $Z_{patient}(t)$ waveforms yielding a set of integral values $\int Z_{patient}(t)dt$, one for each of the stimulation vectors.

These integral values or cardiac performance indices can be acquired over specific time frames. By way of example, the limits for integration can be between time of aortic valve opening and aortic valve closure, so as to derive an index of systolic cardiac performance. Likewise, a diastolic cardiac performance index can be derived during the time frame between aortic valve closure and end-diastole. Any number of indices may be derived and compared using impedance data and those discussed in this invention are by way of example. Other such indices are described in U.S. Pat. No. 7,010,347. In some implementations, it may be appropriate to use line integrals.

At step 308, the pacer/ICD then compares $\int Z_{patient}(t)dt$ against $\int Z_{eucontractile}(t)dt$ for each stimulation vector and makes adjustments to the inotropic pulse parameters associated with any or all stimulation vectors in an attempt to reduce arithmetic differences between $\int Z_{patient}(t)dt$ and $\int Z_{eucontractile}(t)dt$ along the various stimulation vectors, such as an area difference between the integrals (e.g. minimal integral difference). A variety of otherwise conventional mathematic techniques may be used to quantify the difference between or among the various dynamic impedance waveforms along the various stimulation vectors. Processing then returns to step 304 where additional inotropic stimulation is delivered using the adjusted set of parameters. Steps 304-308 proceed in a loop to repeatedly and iteratively adjust the inotropic parameters in an effort to improve patient contractility by reducing the degree of incongruence between $\int Z_{patient}(t)dt$ and $\int Z_{eucontractile}(t)dt$ along the various stimulation vectors. Thus, again, an iterative and adaptive procedure is provided for optimizing inotropic stimulation parameters. As with the technique of FIG. 3, the pacer/ICD is preferably programmed to select different stimulation vectors for delivery of the inotropic stimulation during initial iterations of the procedure so as to identify the particular stimulation vectors that have the greatest affect on contractility. Once the optimal stimulation vector(s) has been identified, the other parameters defining the inotropic stimulation pulse are then iteratively and adaptively adjusted to refine the efficacy of the pulses.

Figure 5:
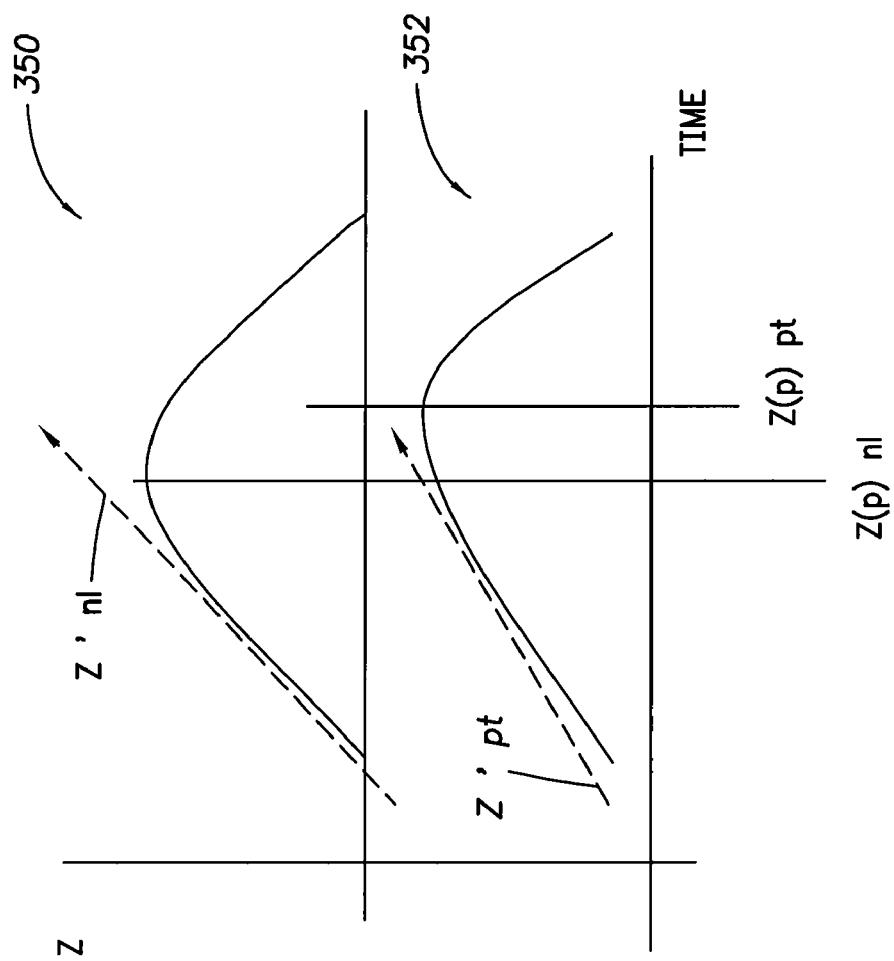
FIG. 5 is a graph illustrating derivative-based impedance parameters that may also be exploited using the techniques of FIGS. 1-4.

Additionally, or alternatively, derivatives of the dynamic impedance waveform may be exploited to determine optimal inotropic parameters. Exemplary derivatives are illustrated in FIG. 5. Briefly, the figure illustrates first and second impedance waveforms 350 and 352. Waveform 350 is that of a normal i.e. healthy person (nl). Waveform 352 is that of a patient with some dysfunction. As can be seen, the first derivative of Z (t) dt in the patient, (Z' pt) differs from that of the normal individual, (Z' nl). Additionally, the time of peak Z, (Z p), occurs later and with a lower peak value during the cardiac cycle in the patient as opposed to the normal waveform. Thus, one can detect impairments in contractility and timing using impedance based indices. U.S. Pat. No. 7,010,347 provides more examples of how impedance based indices provide insight into such pathophysiology.

Figure 6:
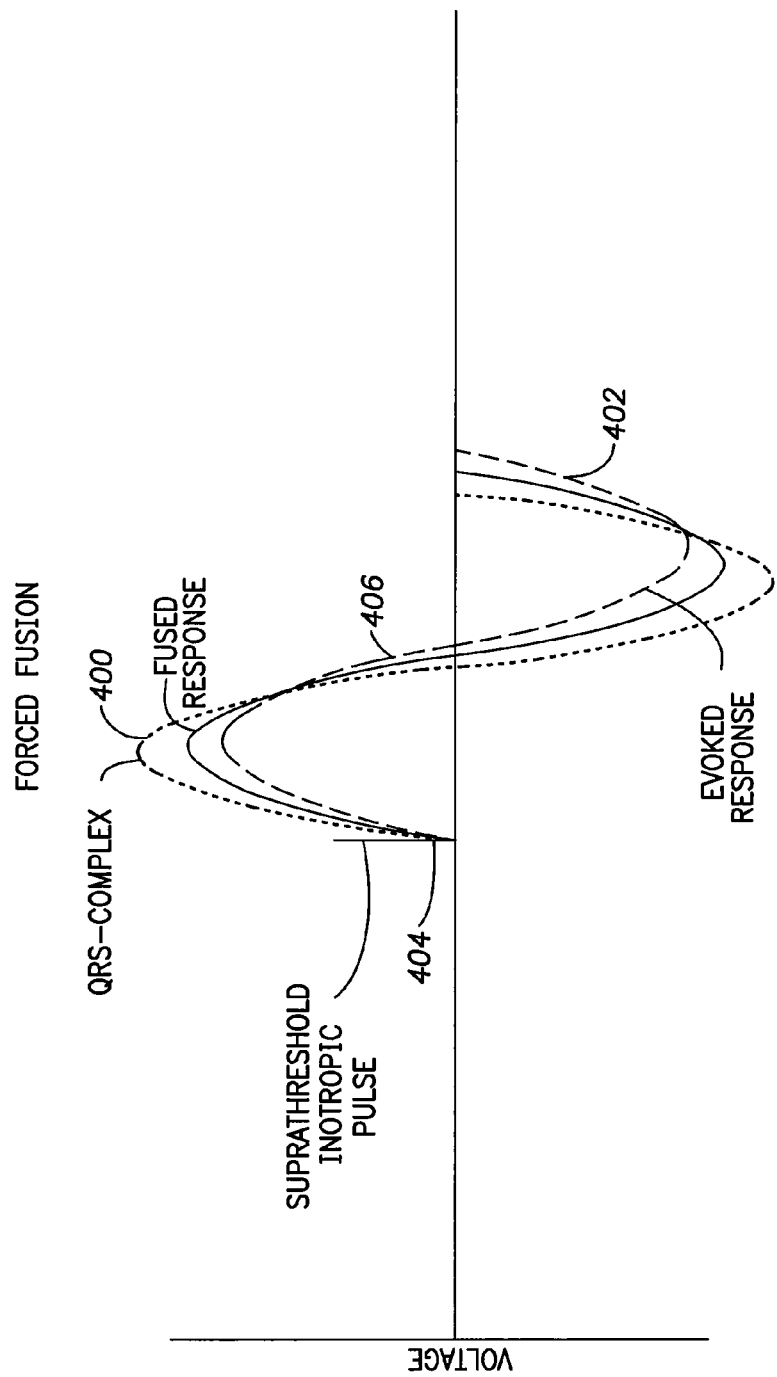
FIG. 6 is a graph illustrating forced fusion, which may be achieved using the techniques of FIGS. 1-5.

The aforementioned techniques may be advantageously employed to determine a set of inotropic parameters sufficient to achieve forced fusion between intrinsic depolarization and evoked responses triggered by inotropic pulses. Forced fusion is illustrated in FIG. 6 between a QRS-complex 400 associated with an intrinsic depolarization of the ventricles and an evoked response 402 triggered by a suprathreshold inotropic stimulation pulse 404. As can be seen, the resulting voltage waveform 406 represents a fusion of the two separate voltage waveforms. Although not shown, the resulting dynamic impedance waveform represents a fusion between the dynamic impedance waveform associated with the intrinsic depolarization and the dynamic impedance waveform associated with inotropic pulse. Forced fusion is most readily achieved by timing the delivery of the regional suprathreshold inotropic pulse 404 with the start of the global QRS-complex so that portions of the myocardium contract in response to the intrinsic depolarization and other portions contract in response to the inotropic pulse. It is believed that forced fusion is particularly effective technique for changing the dynamic impedance waveform of the patient to more closely match the eucontractile dynamic impedance waveform since different portions of the myocardium contract in response to different electrical signals. Note also that, by applying high frequency, inotropic, subthreshold stimuli as well as suprathreshold, depolarization stimulation pulses along multiple stimulation vectors at varying time delays, a form of "multi-dimensional fusion" can thereby achieved, temporally and spatially, i.e. MDF is achieved. One means for verifying appropriate temporal delivery of stimuli is by analyzing relative differences in regional times of peak impedance, Z p as described in detail in U.S. Pat. No. 7,010,347. Thus, the impedance curves provide insight into properties of contractility and timing.

Note also that the techniques of either FIG. 3 or FIG. 4 may be used to determine the appropriate stimulation vector(s) and to optimize the specific timing(s) of the suprathreshold inotropic pulse(s) relative to the start of the intrinsic depolarization, as well as to optimize other parameters defining the inotropic pulse such as voltage and polarization. This suprathreshold pulse serves to depolarize myocardium at the appropriate time and is rendered inotropic when accompanied by some form of NPIT as described in more detail below.

Multiple Pre- and Post-Systolic Subthreshold Inotropic Pulses

Figure 7:
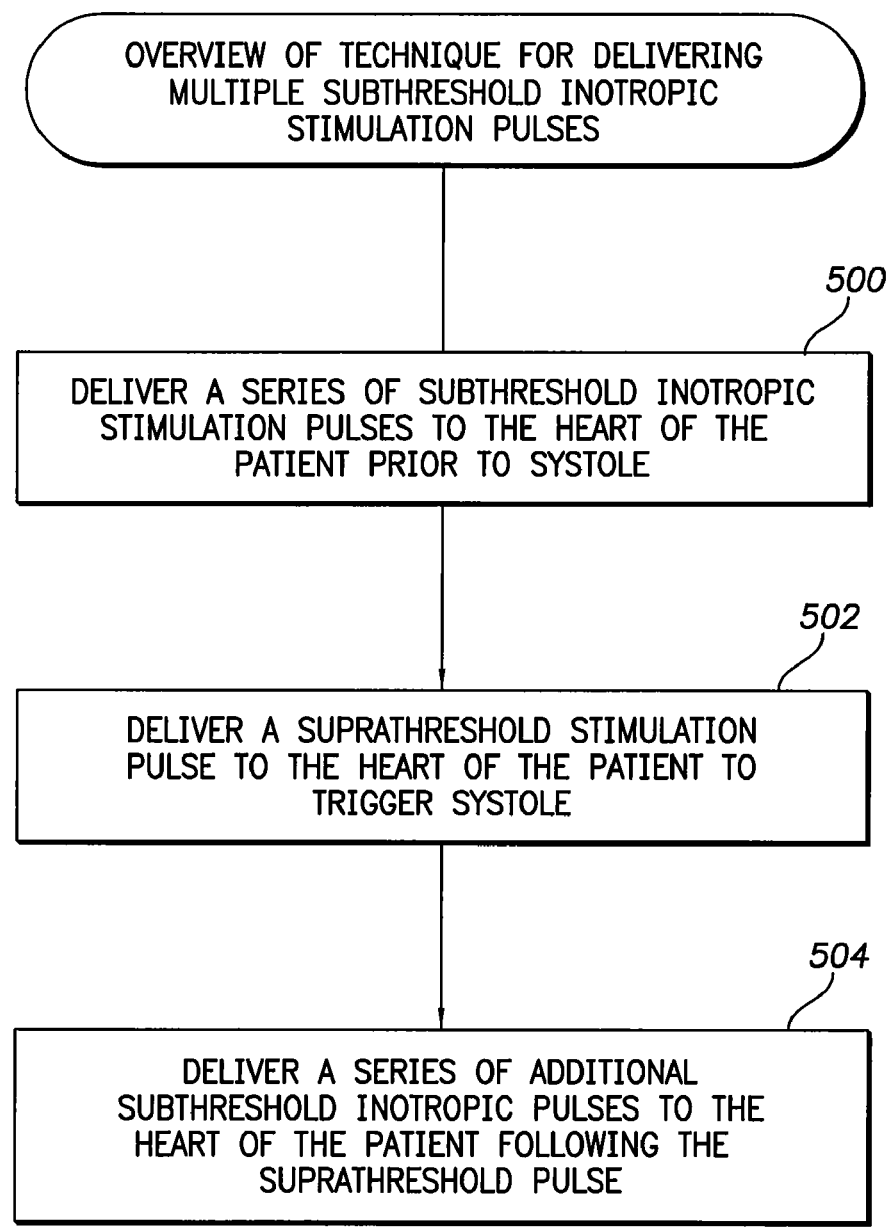
FIG. 7 is a flow chart providing an overview of a general technique for delivering multiple subthreshold inotropic stimulation pulses.
Figure 8:
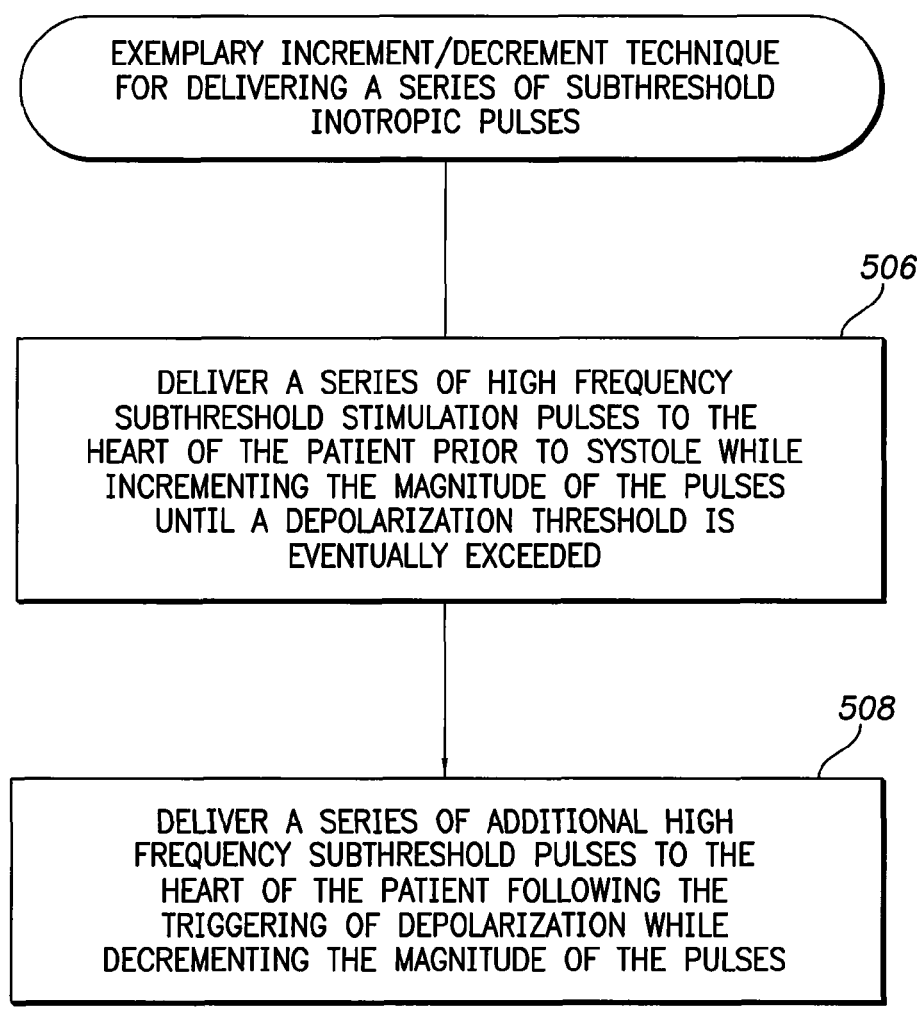
FIG. 8 is a flow chart illustrating an exemplary technique for delivering multiple subthreshold inotropic stimulation pulses, in which magnitudes of the pulses are incrementally increased, then decreased.
Figure 9:
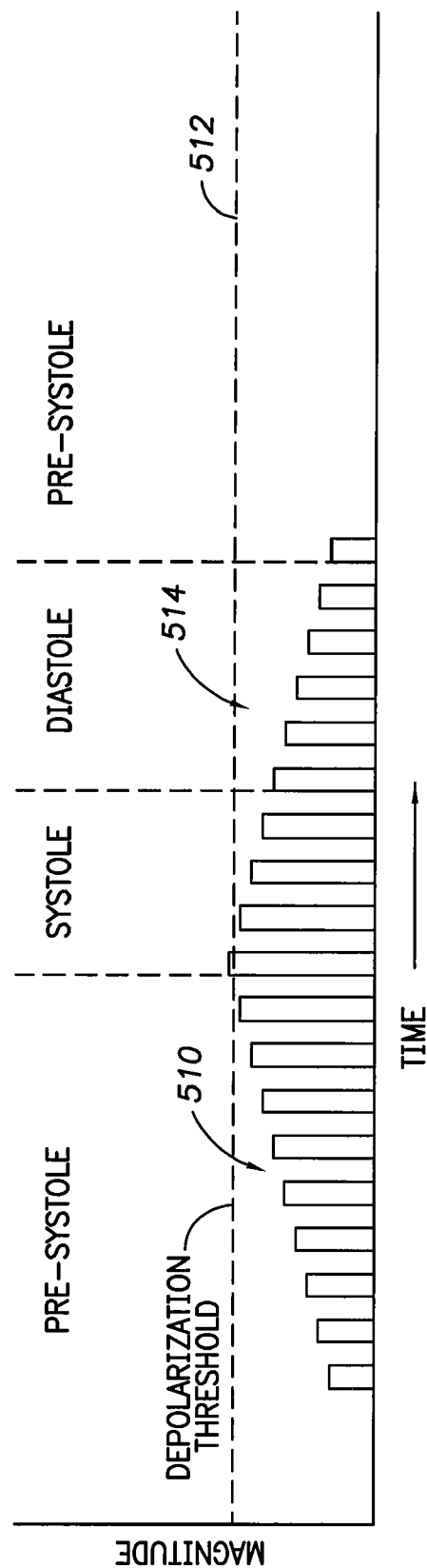
FIG. 9 is a graph illustrating the incremental adjustment technique of FIG. 8.

Turning now to FIGS. 7-9, a technique for delivering a series of pre-systolic and post-systolic inotropic subthreshold pulses will be described. FIG. 7 provides an overview of one example of the technique, which is performed by a pacer/ICD or other implantable cardiac stimulation devices. Beginning at step 500, the pacer/ICD delivers a series of subthreshold inotropic stimulation pulses to the heart of the patient prior to systole, i.e. prior to depolarization of the ventricles. At step 504, the pacer/ICD delivers a suprathreshold stimulation pulse to the heart of the patient to trigger ventricular systole, i.e. a V-pulse is delivered. At step 506, the pacer/ICD then delivers a series of additional subthreshold inotropic pulses to the heart following the suprathreshold pulse. These pulses may extend through systole and into diastole. It is believed that a series of subthreshold pulses delivered before and/or after a V-pulse is effective for mitigating hypocontractility. Preferably, the pulses are high-frequency pulses having incrementally varying pulse magnitudes. This is summarized in FIG. 8 and illustrated in FIG. 9.

At step 506 of FIG. 8, the pacer/ICD delivers a series of high-frequency subthreshold stimulation pulses to the heart of the patient prior to systole while incrementing the magnitude of the pulses until a depolarization threshold is eventually exceeded. By high frequency, it is meant that the pulses have frequency components significantly higher than those associated with conventional pacing pulses. In one example, current pulses having a high frequency AC component are employed, similar to the current pulses conventionally used to measure impedance. However, whereas conventional impedance measurement pulses (IMPs) do not have magnitudes sufficient to trigger depolarization, the pulses delivered during step 506 eventually exceed a magnitude sufficient to trigger depolarization. In a preferred embodiment, the same pulses used to improve contractility are implemented for determining impedance values as to generate Z (t) dt. Such pulses may or may not be varying in magnitude and can be equivalent in amplitude and even have incremental and/or decremental pulse widths. At step 508, the pacer/ICD delivers a series of additional high frequency subthreshold pulses to the heart of the patient following the triggering of depolarization, while decrementing the magnitude of the pulses.

FIG. 9 illustrates the inotropic pulse train generated by the technique of FIG. 8. A first series of high frequency inotropic pulses 510 are delivered prior to systole and have incrementally increasing pulse magnitudes. The high frequency components are not specifically shown in the figure; rather the overall pulse shape is instead shown. In addition, to minimize current drain from the power supply of the pacer/ICD, the direction of overall current flow may be alternated during each pulse, as with IMPs. In any case, the pulse magnitude increases until a depolarization threshold 512 is exceeded, thus triggering depolarization (not shown). Thereafter, a second series of high frequency inotropic pulses 514 are delivered during systole and into diastole, with incrementally decreasing pulse magnitudes. Note that the width of the pulses may be varied as well to, e.g., make the pulses wider near the suprathreshold pulse. In addition, individual pulses may be applied using different stimulation vectors.

In one example, the frequency of the inotropic stimulation pulses is in the range of 16 to 256 Hz and pulse widths are in the range of 0.5-20 ms. (E.g., a 10 ms pulse delivered at 50 Hz.) The total number of inotropic stimulation pulses delivered prior to depolarization should be adequate to achieve inotropy without excessive costs to the system (e.g. battery depletion). By way of example, the total number of inotropic stimulation pulses delivered before and/or following depolarization is in the range of 1 to 100 pulses. The magnitude of the weakest of the inotropic stimulation pulses, expressed as a percentage of a depolarization threshold voltage for the patient, may be in the range of 12.5 to 87.5%. The first set of incrementally increasing subthreshold pulses are preferably delivered just prior to the suprathreshold pulse. Likewise, the second set of incrementally decreasing (i.e. decrementing) subthreshold pulses are preferably delivered just following to the suprathreshold pulse. In one example, all of the first set of subthreshold pulses are delivered within a time period extending 100 milliseconds prior to the suprathreshold pulse. All of the second set of subthreshold pulses are delivered within a time period extending 100 milliseconds following the suprathreshold pulse. Note also, that in some examples, it may be appropriate to only deliver subthreshold pulses prior to the suprathreshold pulse. In other examples, it may be appropriate to only deliver subthreshold pulses following to the suprathreshold pulse. Hence, the example wherein subthreshold pulses are delivered both prior to and after the suprathreshold represents just one implementation and various characteristics and durations of such pulse trains may be optimal in different clinical scenarios. In some implementations, the pre- and post-pulses are inotropic pulses whereas the pulse that triggers depolarization is a more typical 0.1-2 ms duration pulse. The duration of the pulse train is not necessarily inclusive of (or not necessarily exclusive of) the absolute and relative refractory periods. Pulse widths can be decremented and/or incremented along with changes in the amplitude or magnitude of the stimuli.

The techniques described above with reference to FIGS. 1-6 may be advantageously exploited to optimize these and other parameters defining the inotropic pulse train of FIGS. 7-9, including determining the optimal stimulation vector for delivering the pulse train, the starting pulse magnitudes, the pulse increments, the start and stop times, etc. In particular, the use of a pulse train represents a particularly effective technique for generated forced fusion. In this regard, the incremental increase in pulse magnitude allows gradual recruitment of myocardial tissue (i.e. incremental myocardial recruitment (IMR)). This technique is of particular value as the lower magnitude stimuli will depolarize tissue that has a lower threshold for depolarization and the greater magnitude stimuli will depolarize tissue that has higher thresholds for depolarization (e.g. from scarring). Thus, tissue that may normally not be recruited from lower magnitude stimulation is depolarized. Suprathreshold stimuli for certain myofibrils may be sub-threshold for others. Delivery of higher magnitude stimulation will allow recruitment of tissue that would otherwise be dormant. Preliminary data suggests that higher energy left ventricular pacing may be more effective than delivering pacing voltages that only ensure capture of the "left ventricle" as a whole entity. Thus, specific regions that are pathologic may be recruited and depolarize from higher energy impulses (or the additive effect of sub-threshold pulse trains) and the end-result is better overall contractility. The high frequency drive train also serves to augment contractility to regions that are effectively depolarized from supra-threshold stimulation. Thus, although sub-threshold stimulation may not depolarize all myocardium in a specific region, it will likely serve to increase contractility once a regionally suprathreshold stimulus arrives.

Note that this is somewhat contrary to the principle that myocardial depolarization is "all or none". Indeed for any region of myocardium (e.g. individual myofibrils) once depolarization occurs, contraction ensues and neighboring myofibrils depolarize secondary to being a conductive tissue (via gap junctions that electrically connect neighboring myofibrils.) However, it is believed by the inventor that not all regions necessarily depolarize simultaneously, as specific areas may have high pacing thresholds and/or are electrically isolated secondary to scar tissue. Although late depolarized regions may indeed contract (assuming the tissue is not electrically isolated or dead), the myofibrils may contract so late during the cardiac cycle (i.e. dysynchronous contraction) as to be a detriment and not contribute to global systole. MDF is, at least in part, intended to rectify this pathologic state by augmenting contraction in myocardium that is depolarized and ensuring depolarization of myocardium that has high pacing thresholds and/or is electrically isolated enough to either not be depolarized or be depolarized so late that there is no contribution to global systole. The use of different stimulation vectors allows the gradual recruitment to proceed from different directions to encourage forced fusion. The pulse trains are preferably applied during each heart beat to remodel the myocardium over time, but may be applied at periodic intervals or on an "as needed" basis. Note that, regardless of whether "all or none" depolarization does indeed occur, the techniques of the invention are believed to have advantageous effects.

Thus, FIGS. 1-9 illustrate various inotropic stimulation techniques. In other embodiments, rather than comparing patient impedance waveforms against eucontractile waveforms obtained from healthy patients, the implanted device instead compares newly detected impedance waveforms within the patient against previously detected impedance waveforms within the same patient. That is, the inotropic stimulation parameters do not necessarily need to be based on $Z_{eucontractile}(t)$ but can instead be based on monitoring changes in any impedance based metric while the pacing modalities described herein are active and comparing this to baseline data acquired from the patient while such pacing modalities are inactive. In still other embodiments, a direct comparison of one impedance waveform against another is not performed. Rather, the implanted device instead seeks to modify stimulation patterns to achieve optimal values of any specific impedance-based index. For example, for electrode combinations that traverse the LV (interventricular septal to LV lateral electrodes), the greater the Z(t) dt value is during cardiac systole, the greater the contractility/systolic cardiac performance.

Although described primarily with reference to ventricular stimulation examples, atrial inotropic stimulation may alternatively or additionally be employed. The various techniques may be exploited using any appropriate implantable cardiac stimulation device. For the sake of completeness, an exemplary pacer/ICD will now be described.

Exemplary Pacemaker/ICD

Figure 10:
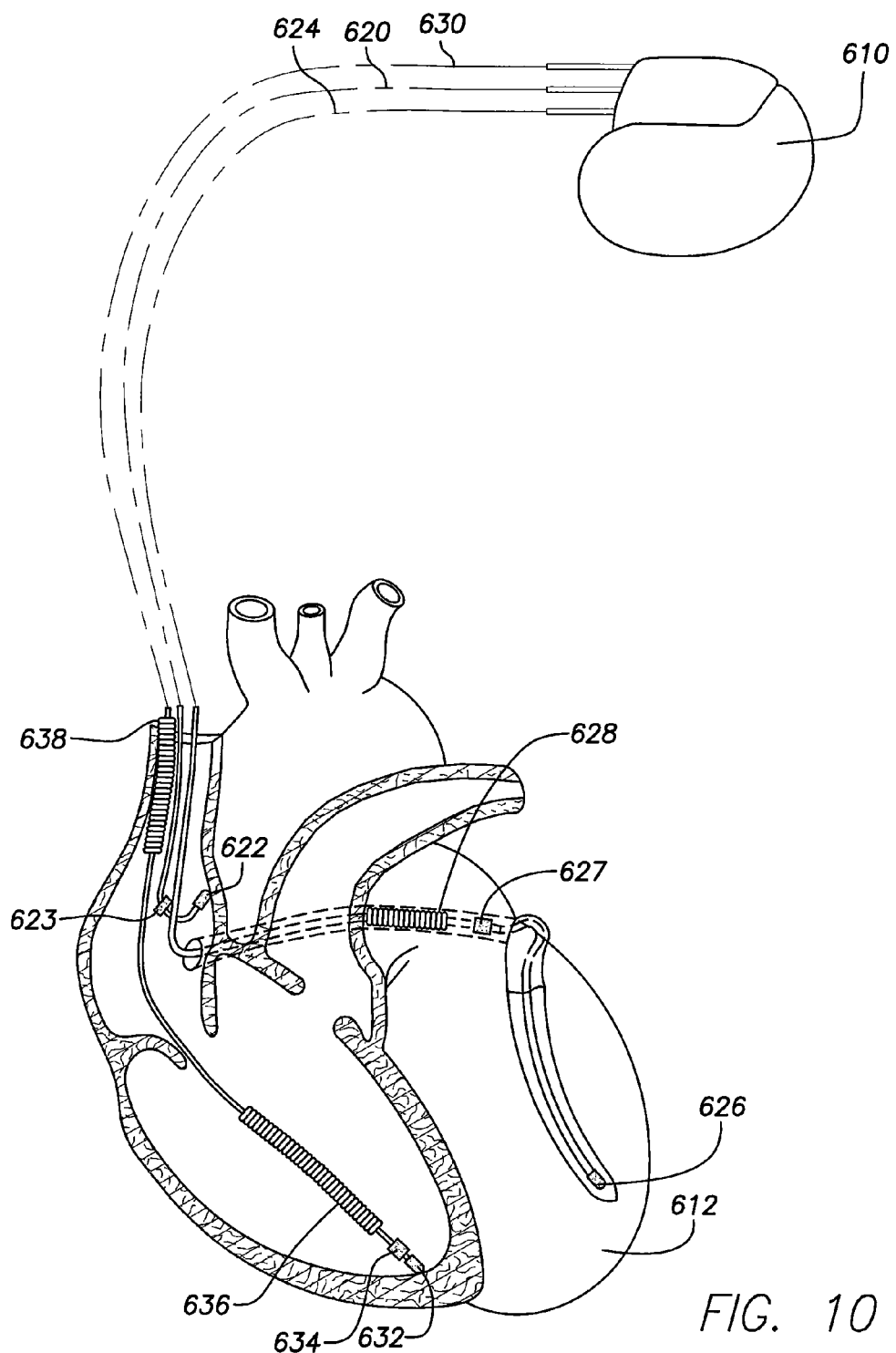
FIG. 10 is a simplified, partly cutaway view, illustrating a pacer/ICD that maybe configured to implement the techniques of FIGS. 1-9, along with a set of leads implanted in the heart of a patient.

FIG. 10 provides a simplified block diagram of the pacer/ICD, which is a multi-chamber stimulation device capable of treating both fast and slow arrhythmias with stimulation therapy, including cardioversion, defibrillation, and pacing stimulation, as well as being capable of delivering inotropic stimulation using the techniques of FIGS. 1-9. To provide atrial chamber pacing stimulation and sensing, pacer/ICD 610 is shown in electrical communication with a heart 612 by way of a left atrial lead 620 having an atrial tip electrode 622 and an atrial ring electrode 623 implanted in the atrial appendage. Pacer/ICD 610 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 610 is coupled to a "coronary sinus" lead 624 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. (To the extent that atrial pacing is relevant to the invention, the examples herein pertain to right atrial pacing/sensing but left atrial pacing/sensing may also be used.) With this configuration, biventricular pacing can be performed. Although only three leads are shown in FIG. 10, it should also be understood that additional stimulation leads (with one or more pacing, sensing and/or shocking electrodes) may be used in order to efficiently and effectively provide pacing stimulation to the left side of the heart or atrial cardioversion and/or defibrillation. The leads are also employed for sensing patient dynamic impedance waveforms and for delivering inotropic stimulation.

Figure 11:
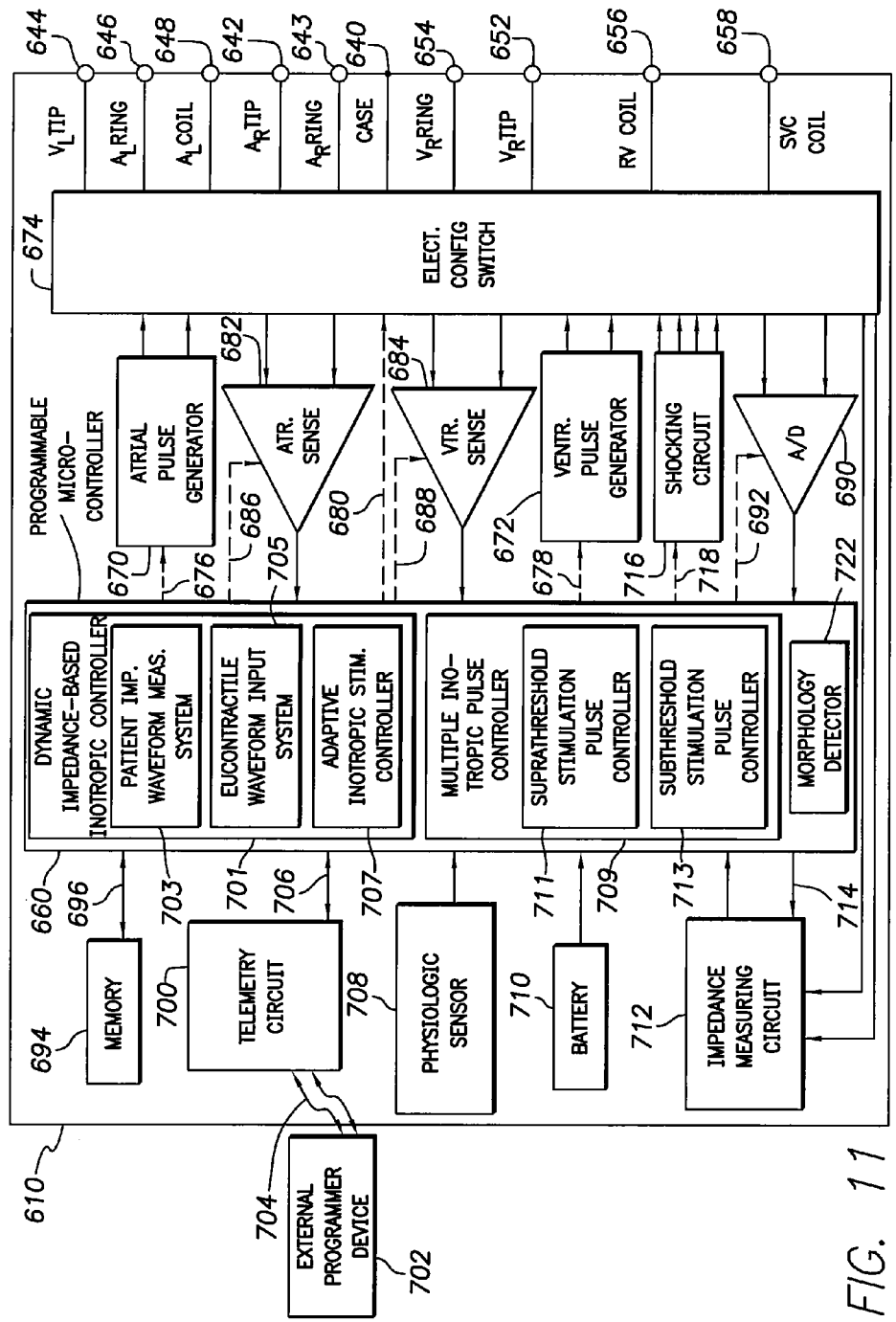
FIG. 11 is a functional block diagram of the pacer/ICD of FIG. 10, illustrating basic circuit elements that provide cardioversion, defibrillation and/or pacing stimulation in four chambers of the heart and particularly illustrating components for controlling the functions of FIGS. 1-9.

A simplified block diagram of internal components of pacer/ICD 610 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 640 for pacer/ICD 610, shown schematically in FIG. 11, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 643. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 632, right ventricular ring electrode 634, the RV coil electrode 636, and the SVC coil electrode 638, respectively.

At the core of pacer/ICD 610 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code (i.e. software) stored in a designated block of memory. Software running within the microcontroller 60 includes various components for controlling the functions described above in connection with FIGS. 1-9. These components are illustrated as functional components of the microcontroller. Depending upon the implementation, the various components of the microcontroller may be implemented as separate software or hardware modules. However, the modules may be combined to permit single modules to perform multiple functions.

In particular, the microcontroller includes a dynamic impedance-based inotropic stimulation controller 701 operative to control delivery of inotropic therapy based on dynamic impedance waveforms in accordance with the techniques of FIGS. 1-6. The dynamic impedance-based stimulation controller, in turn, includes a patient waveform measurement system 703 operative to obtain information pertaining to dynamic impedance waveforms derived from within the heart of the patient; an eucontractile waveform input system 705 operative to input template information pertaining to dynamic impedance waveforms within healthy hearts; and an adaptive stimulation controller 707 operative to control delivery of electrical stimulation to the heart of the patient based on a comparison of the dynamic impedance waveforms within the heart of the patient and the dynamic impedance waveforms within healthy persons. The microcontroller also includes a multiple inotropic pulse controller 709 having a suprathreshold stimulation controller 711 operative to deliver an appropriately timed suprathreshold electrical stimulation pulse sufficient to depolarize myocardial tissue within the heart; and a subthreshold stimulation controller 713 operative to deliver a series of subthreshold stimulation pulses to the heart of the patient prior to delivery of the suprathreshold pulse and/or to additionally deliver a plurality of subthreshold stimulation pulses following the suprathreshold pulse, generally in accordance with the techniques of FIGS. 7-9.

The details of the design of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 11, an atrial pulse generator 670 and a ventricular pulse generator 672 generate pacing stimulation pulses, impedance detection pulses and inotropic pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the pulses.

The microcontroller 660 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain/sensitivity control enables pacer/ICD 610 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 610 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external programmer device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 610 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate. Still other parameters are the aforementioned inotropic pulse parameters.

Advantageously, the operating parameters of the implantable pacer/ICD 610 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 610 (as contained in the microcontroller 660 or memory 694) to be sent to the external device 702 through an established communication link 704. Pacer/ICD 610 further includes an accelerometer or other physiologic sensor 708, commonly referred to as a "rate-responsive" sensor because it is typically used to adjust pacing stimulation rate according to the exercise state of the patient. However, the physiological sensor 708 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV Delay, V-V Delay, etc.) at which the atrial and ventricular pulse generators, 670 and 672, generate stimulation pulses. While shown as being included within pacer/ICD 610, it is to be understood that the sensor 708 may also be external to pacer/ICD 610, yet still be implanted within or carried by the patient. A common type of rate responsive sensor is an activity sensor incorporating an accelerometer or a piezoelectric crystal, which is mounted within the housing 640 of pacer/ICD 610. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 11. The battery 710 may vary depending on the capabilities of pacer/ICD 610. If the system only provides low voltage therapy, a lithium iodine or lithium copper fluoride cell may be utilized. For pacer/ICD 610, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, pacer/ICD 610 is preferably capable of high voltage therapy and batteries or other power sources appropriate for that purpose are employed.

As further shown in FIG. 11, pacer/ICD 610 is shown as having an impedance measuring circuit 712 which is enabled by the microcontroller 660 via a control signal 714. Impedance measuring circuit 712 detects the dynamic impedance waveforms within the patient. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening and closing of heart valves, etc. The impedance measuring circuit 120 is advantageously coupled to the switch 74 so that any desired electrode pair may be used.

In the case where pacer/ICD 610 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

What have been described are various systems and methods for use with a pacer/ICD. However, principles of the invention may be exploiting using other implantable systems or in accordance with other techniques. Thus, while the invention has been described with reference to particular exemplary embodiments, modifications can be made thereto without departing from the spirit and scope of the invention. Note also that the term "including" as used herein is intended to be inclusive, i.e. "including but not limited to."

What is claimed is:

1. A method for delivering electrical stimulation to the heart of a patient using an implantable medical device, the method comprising:
   measuring information representative of dynamic impedance waveforms within the heart of the patient;
   retrieving information representative of dynamic impedance waveforms within healthy hearts from a memory device for input into a processing device;
   comparing the information representative of dynamic impedance waveforms within the heart of the patient and like information representative of dynamic impedance waveforms within healthy hearts; and
   controlling delivery of electrical stimulation to the heart of the patient to reduce a difference between the dynamic impedance waveforms within the heart of the patient and the dynamic impedance waveforms within healthy hearts; wherein the stimulation comprises applying relatively high frequency, inotropic, subthreshold stimuli along with suprathreshold, depolarization stimulation pulses along multiple stimulation vectors at varying time delays to trigger localized depolarizations that fuse with intrinsic depolarization to affect both spatial and temporal aspects of myocardial electro-mechanical activation within the heart of the patient.

2. The method of claim 1 wherein measuring information representative of dynamic impedance waveforms within the heart of the patient includes
   delivering electrical stimulation to the heart of the patient while varying parameters defining the characteristics of the electrical stimulation to acquire resulting dynamic impedance waveforms; and
   wherein comparing the information includes comparing the resulting dynamic impedance waveforms within the patient against dynamic impedance waveforms of healthy hearts to determine electrical stimulation parameters that reduce a difference between the resulting dynamic impedance waveforms and the dynamic impedance waveforms of healthy hearts.

3. The method of claim 2 wherein varying parameters defining the characteristics of the electrical stimulation includes varying one or more of stimulation voltage, current, polarity, timing and direction.

4. The method of claim 3 wherein the implantable device includes a plurality of stimulation electrodes and wherein stimulation direction is varied by selecting different pairs of the stimulation electrodes for delivering the stimulus so as to select different stimulation vectors.

5. The method of claim 2 wherein controlling the delivery of electrical stimulation to the heart of the patient includes controlling the delivery of one or more of subthreshold stimulation pulses and suprathreshold stimulation pulses.

6. The method of claim 5 wherein controlling the delivery of electrical stimulation to the heart of the patient includes
   delivering a series of subthreshold stimulation pulses while incrementing respective magnitudes of individual pulses in the series of pulses up to a suprathreshold depolarization stimulus magnitude and then decrementing the respective magnitudes of the individual pulses in the series of pulses.

7. The method of claim 2 wherein the information representative of dynamic impedance waveforms represents impedance as a function of time ($Z(t)$).

8. The method of claim 7
wherein measuring information representative of dynamic impedance waveforms includes measuring resulting dynamic impedance waveforms ($Z_{patient}(t)$) within the patient; and
wherein retrieving information representative of dynamic impedance waveforms within the healthy hearts includes retrieving a template representative of dynamic eucontractile impedance waveforms ($Z_{eucontractile}(t)$) measured within the healthy hearts.

9. The method of claim 8 wherein comparing the information representative of dynamic impedance waveforms within the heart of the patient and like information representative of dynamic impedance waveforms within healthy hearts includes:
comparing $Z_{patient}(t)$ against $Z_{eucontractile}(t)$ to determine parameters that minimize an average difference between $Z_{patient}(t)$ and $Z_{eucontractile}(t)$ throughout delivery of the stimulus.

10. The method of claim 7 wherein the information representative of dynamic impedance waveforms represents an integral of impedance as a function of time (Z(t)), the integral limits taken over any pre-specified time frame during the cardiac cycle.

11. The method of claim 10 where said time frame includes one or more of cardiac systole and cardiac diastole so as to derive indices representative of one or more of systolic and diastolic cardiac performance.

12. The method of claim 10
wherein measuring information representative of dynamic impedance waveforms includes measuring dynamic impedance waveforms ($Z_{patient}(t)$) within the patient and calculating integrals of the measured dynamic impedance waveforms ($\int Z_{patient}(t)dt$); and
wherein retrieving information representative of dynamic impedance waveforms within healthy hearts includes retrieving integrals ($\int Z_{eucontractile}(t)dt$) derived from dynamic impedance waveforms ($Z_{eucontractile}(t)$) measured within healthy hearts.

13. The method of claim 12 wherein comparing the information representative of dynamic impedance waveforms within the heart of the patient and like information representative of dynamic impedance waveforms within healthy hearts includes:
comparing $\int Z_{patient}(t)dt$ against $\int Z_{eucontractile}(t)dt$ to determine parameters that minimize a difference between $\int Z_{patient}(t)dt$ and $\int Z_{eucontractile}(t)dt$ over the time period of delivery of the stimulus.

14. The method of claim 13 wherein comparing $\int Z_{patient}(t)dt$ against $\int Z_{eucontractile}(t)dt$ to determine parameters that minimize a difference between $\int Z_{patient}(t)dt$ and $\int Z_{eucontractile}(t)dt$ over the time period of delivery of the stimulus is performed to minimize a difference between the integrals.

15. The method of claim 7
wherein measuring information representative of dynamic impedance waveforms includes measuring one or more of first and second order derivatives of the dynamic impedance waveforms within the patient; and
wherein retrieving information representative of dynamic impedance waveforms within healthy hearts includes retrieving corresponding derivatives derived from dynamic impedance waveforms ($Z_{eucontractile}(t)$) measured within healthy hearts.

16. The method of claim 1 wherein controlling the delivery of electrical stimulation to the heart of the patient includes
controlling the delivery of stimulus having characteristics selected so as to increase contractility of the stimulated myocardium.

17. The method of claim 1 wherein the delivery of stimulation further comprises:
delivering a plurality of subthreshold stimulation pulses to the heart of the patient;
delivering a suprathreshold stimulation pulse to the heart of the patient to trigger systole; and
wherein the plurality of subthreshold stimulation pulses are delivered during one or more of a time period prior to delivery of the suprathreshold pulse or a time period following delivery of the suprathreshold pulse.

18. The method of claim 17 wherein delivery of the plurality of subthreshold stimulation pulses is timed so as not to be proarrhythmic.

19. The method of claim 17 wherein the subthreshold stimulation pulses are high-frequency pulses having a frequency substantially higher than a frequency of conventional pacing pulses.

20. The method of claim 17 wherein a frequency of the subthreshold stimulation pulses is in the range of 16 to 256 Hz.

21. The method of claim 17 wherein a total number of subthreshold stimulation pulses is in the range of 1 to 100 pulses.

22. The method of claim 17 wherein the time period prior to delivery of the suprathreshold pulse is a time period within 100 milliseconds prior to the suprathreshold pulse.

23. The method of claim 17 wherein the time period following delivery of the suprathreshold pulse is a time period within 100 milliseconds following the suprathreshold pulse.

24. The method of claim 17 wherein a first plurality of subthreshold pulses are delivered just prior to the suprathreshold pulse and a second plurality of pulses are delivered just following the suprathreshold pulse.

25. The method of claim 24
wherein delivering the first plurality of subthreshold stimulation pulses are delivered while incrementing a magnitude of the pulses until a depolarization threshold is eventually exceeded thereby providing said suprathreshold pulse; and
wherein delivering the second plurality of subthreshold stimulation pulses are delivered while decrementing a magnitude of the pulses.

26. The method of claim 25 wherein the magnitude of the subthreshold stimulation pulses that is adjusted is a peak voltage magnitude.

27. The method of claim 26 wherein the magnitude of the weakest of the stimulation pulses, as a percentage of a depolarization threshold voltage for the patient, is in the range of 12.5 to 87.5%.

28. A system for delivering electrical stimulation to the heart of a patient using an implantable medical device, the system comprising:
a measurement system operative to measure information representative of dynamic impedance waveforms within the heart of the patient;
a retrieval system operative to retrieve information representative of dynamic impedance waveforms within healthy hearts from a memory device for input into a processing device;
a comparison system operative to compare the information representative of dynamic impedance waveforms within the heart of the patient and like information representative of dynamic impedance waveforms within healthy hearts; and a stimulation controller operative to control delivery of electrical stimulation to the heart of the patient to reduce a difference between the dynamic impedance waveforms within the heart of the patient and the dynamic impedance waveforms of healthy hearts; wherein the stimulation comprises applying relatively high frequency, inotropic, subthreshold stimuli along with suprathreshold, depolarization stimulation pulses along multiple stimulation vectors at varying time delays to trigger localized depolarizations that fuse with intrinsic depolarization to affect both spatial and temporal aspects of myocardial electro-mechanical activation within the heart of the patient.

29. A system for delivering electrical stimulation to the heart of a patient using an implantable medical device, the system comprising:

means for measuring information representative of dynamic impedance waveforms within the heart of the patient;

means for retrieving information representative of dynamic impedance waveforms within healthy hearts from a memory device for input into a processing device;

means for comparing the information representative of dynamic impedance waveforms within the heart of the patient and like information representative of dynamic impedance waveforms within healthy hearts; and means for controlling delivery of electrical stimulation to the heart of the patient to reduce a difference between the dynamic impedance waveforms within the heart of the patient and the dynamic impedance waveforms within healthy hearts; wherein the stimulation comprises applying relatively high frequency, inotropic, subthreshold stimuli along with suprathreshold, depolarization stimulation pulses along multiple stimulation vectors at varying time delays to trigger localized depolarizations that fuse with intrinsic depolarization to affect both spatial and temporal aspects of myocardial electro-mechanical activation within the heart of the patient.

* * * * *